United States Patent
Fischer

(10) Patent No.: US 9,867,892 B2
(45) Date of Patent: Jan. 16, 2018

(54) AQUEOUS CLEANSER FOR DENTAL APPLIANCES

(71) Applicant: Beth Fischer, Suffern, NY (US)

(72) Inventor: Beth Fischer, Suffern, NY (US)

( * ) Notice: Subject to any disclaimer, the term of this patent is extended or adjusted under 35 U.S.C. 154(b) by 0 days.

(21) Appl. No.: 14/765,051

(22) PCT Filed: Jan. 31, 2014

(86) PCT No.: PCT/US2014/014154
§ 371 (c)(1),
(2) Date: Jul. 31, 2015

(87) PCT Pub. No.: WO2014/121074
PCT Pub. Date: Aug. 7, 2014

(65) Prior Publication Data
US 2015/0374866 A1    Dec. 31, 2015

Related U.S. Application Data

(60) Provisional application No. 61/759,511, filed on Feb. 1, 2013.

(51) Int. Cl.
| | | |
|---|---|---|
| A61Q 11/02 | (2006.01) |
| A61Q 11/00 | (2006.01) |
| A61L 2/08 | (2006.01) |
| A61L 2/18 | (2006.01) |
| A61K 8/34 | (2006.01) |
| A61K 8/36 | (2006.01) |
| A61K 8/368 | (2006.01) |
| A61K 8/46 | (2006.01) |
| A01N 37/10 | (2006.01) |

(52) U.S. Cl.
CPC ............. *A61L 2/18* (2013.01); *A01N 37/10* (2013.01); *A61K 8/345* (2013.01); *A61K 8/361* (2013.01); *A61K 8/368* (2013.01); *A61K 8/463* (2013.01); *A61Q 11/02* (2013.01)

(58) Field of Classification Search
CPC ....................................................... A61L 2/18
USPC ........................................................... 422/28
See application file for complete search history.

(56) References Cited

U.S. PATENT DOCUMENTS

| | | | |
|---|---|---|---|
| 4,807,649 A * | 2/1989 | Eoga | A61K 8/042 134/2 |
| 5,624,906 A | 4/1997 | Vermeer | |
| 5,849,269 A | 12/1998 | Burgess et al. | |
| 6,670,312 B2 | 12/2003 | Sugimoto et al. | |
| 6,946,142 B2 | 9/2005 | Chang et al. | |
| 7,458,464 B1 | 12/2008 | Kutsch et al. | |
| 7,462,586 B2 | 12/2008 | Tijanic et al. | |
| 8,044,008 B2 | 10/2011 | Muzik et al. | |
| 2007/0298991 A1 | 12/2007 | Longo, Jr. | |
| 2009/0092561 A1 * | 4/2009 | Lupia | A61K 8/347 424/49 |
| 2009/0130032 A1 | 5/2009 | Brogden et al. | |
| 2009/0324662 A1 * | 12/2009 | Kutsch | A61K 8/345 424/401 |
| 2010/0086498 A1 * | 4/2010 | Haught | A61K 8/19 424/49 |
| 2011/0220154 A1 | 9/2011 | Wetterer | |
| 2016/0008297 A1 * | 1/2016 | Schmaus | A61K 9/0014 424/48 |

FOREIGN PATENT DOCUMENTS

| | | |
|---|---|---|
| EP | 1771081 | 4/2007 |
| EP | 2007387 | 12/2008 |
| EP | 2247278 | 11/2010 |
| WO | 2006065239 | 6/2006 |
| WO | 2007112250 | 10/2007 |
| WO | 2009100281 | 8/2009 |

OTHER PUBLICATIONS

The American Dental Aassociation, Restoring your smile with dentures, May 2012, JADA, 143(5), p. 528.*
International Search Report and Written Opinion dated May 26, 2014, from the corresponding PCT/US2014/014154.

* cited by examiner

*Primary Examiner* — Kevin Joyner
*Assistant Examiner* — Holly M Mull
(74) *Attorney, Agent, or Firm* — Katten Muchin Rosenman LLP

(57) ABSTRACT

An aqueous composition is described herein that is safe, convenient, and effective for cleansing dental appliances. The primary cleansing agent in this composition is a surfactant, which allows for fast and effective cleaning without damaging or discoloring the plastic of the dental appliance. The stable aqueous composition does not require dissolving in a reservoir and may be applied directly to the dental appliance. The aqueous composition is safe for natural teeth and therefore easy to incorporate into a regular oral hygiene routine.

16 Claims, No Drawings

AQUEOUS CLEANSER FOR DENTAL APPLIANCES

TECHNICAL FIELD

The present invention relates to a composition for cleaning dental appliances. More specifically, the present invention relates to an aqueous composition which uses a surfactant to clean plastic dental appliances.

BACKGROUND

A new generation of custom-made plastic dental appliances require new techniques and formulations for maintenance and cleaning These appliances sit directly on the teeth and are worn throughout variable time periods depending on each appliances particular application. These appliances must be cleaned regularly to ensure proper oral hygiene of the user, as well as the cosmetic appearance of the appliance itself.

Difficult, expensive, or time-consuming cleaning techniques impede regular cleaning of the appliances, which leads to soiling of appliances with an accumulation of stains, dental plaque, and dental calculus. A soiled appearance or unpleasant taste or odor can prevent regular use of such appliances, and thus impede the desired result of the appliance's application. Additionally, harsh chemicals and toxic ingredients are not only unnecessary for cleaning these next generation appliances, but are also dangerous to or disfavored by modern dental appliance users and thus impede regular cleansing. Some of these chemicals may also damage the appliances. Various such compositions and methods related to cleaning dental products have been previously disclosed in U.S. Pat. Nos. 5,624,906; 5,849,269; 6,670,312; 6,946,142; 7,458,464; 8,044,008; U.S. Patent Application Ser. No. 2007/0298991 A1; EP1771081 A1; EP2007387 A2; and EP2247278 A2, which are hereby incorporated by reference.

Conventional toothpaste is not appropriate for cleansing these appliances for two reasons. First, toothpastes may contain abrasives that scratch the plastic surfaces of these appliances, causing opacity and structural weakening. These scratches also create ideal locations for bacteria and dental plaque to accumulate. Second, many such dental appliances contain small wells on their surfaces to accommodate various orthodontic components, e.g., attachments used in conjunction with orthodontic aligners, and toothpaste tends to settle and reside inside these wells, making it difficult to remove.

Commercially-available mouthwashes are also unsuitable for cleaning dental appliances, as they may contain dyes and other chemicals, which can discolor the appliances and compromise the appliances' clarity, invisibility and transparency. They may also contain chemicals which may damage the appliances.

Electric sonic and ultrasonic cleaning devices, while thorough, can be expensive, cumbersome, and difficult to transport and may incorporate ultraviolet light elements. Additionally, ultraviolet radiation is utilized in devices, known as uv cases, to sanitize dental appliances. Ultraviolet radiation can, however, weaken, embrittle and discolor the plastic in dental appliances.

Powder, tablet cleansers and crystals while also thorough, can require an outside water source, a reservoir to dissolve the cleanser in, and time to dissolve or effervesce. The dental appliance must sit passively in the reservoir while it is cleaned. While this method is conducive to bathroom counters and nightstands, many modern dental appliances are worn throughout different periods of the day and are best cleansed on the go. Additionally, some powders, tablets and crystals contain highly allergenic persulphates or bleach, and modern dental appliance users prefer that fewer such harsh chemicals are incorporated in their daily oral hygiene routine.

Modern cleaning wipes are expensive and meant for quick, relatively superficial cleaning of an appliance for a user on the go. Sprays typically use larger volumes of product and are not applied with ease. Both wipes and sprays do not target the difficult to reach crevices, wells and indentations within a plastic appliance. Some products are liquid soaking products for cleaning dental appliances using long-term soaking for 1-24 hours in a more concentrated solution or as a diluted solution for shorter soaking periods of 5-10 minutes, or longer, followed by rinsing.

Thus, there exists a need for a safe, simple, effective, and quick cleanser for plastic dental appliances that does not contain harsh chemicals which impede regular use or deteriorate the plastic of the appliances. Ideally this would be in the form of a liquid, paste or a gel which would be easy to use and rinse off. It should also be mild enough to allow utilization of the same toothbrush that the user brushes their teeth with. These characteristics would greatly simplify plastic dental appliance care and maintenance and allow their easy incorporation in to the user's regular oral hygiene routine. This would greatly increase the compliance of patients, in turn increasing the efficacy of treatment.

SUMMARY OF THE INVENTION

The present disclosure is directed to a stable aqueous cleanser of dental appliances that uses a surfactant as a cleansing agent. In one form of the invention the composition comprises water, a surfactant, a flavor additive, a solvent, a preservative, and a buffering agent. In another form of the invention, the composition may additionally include a chelating agent. In another form of the invention, a small amount of dye may be included.

It is an object of the present invention to be effective on many types of dental and orthodontic appliances, such as, but not limited to orthodontic aligners, retainers, nightguards, mouthguards, dentures, and implants. Some of these appliances may be custom made to sit directly on top of the teeth and be shaped like teeth (e.g., dental appliances from impressions), or they may be non-custom, uniformly produced (e.g., certain mouthguards or nightguards). These appliances may also be made to cover only the crowns of the teeth and not the gums or palate (e.g., aligners) and can be made of varying types of plastics including, but not limited to, polyurethane, polypropylene, and polyvinyl chloride.

DETAILED DESCRIPTION

Embodiments of the present invention will be described hereinbelow. In the following description, well-known functions or constructions are not described in detail because they may obscure the invention in unnecessary detail. The present invention relates to an aqueous cleanser for dental appliances that uses a surfactant as its primary cleansing agent.

The present invention is directed to a stable aqueous composition used as a cleanser for dental appliances in which the primary cleansing agent is a surfactant. Neither bleach, peroxides, nor persulphates are used in the present invention. In one of the preferred embodiments, the invention is applied directly to the dental appliance, or to the appliance with an applicator (e.g., toothbrush, cloth or similar implement). The aqueous composition used is preferably bottled in a container with a cap allowing the invention to be repeatedly dispersed in individual drops. The aqueous composition herein can be used to clean dental appliances (e.g., Invisalign® orthodontic aligners and Essix® retainers) worn regularly or daily by users. The aqueous composition is effective at cleaning dental appliances and will result in maintenance of their cosmetic appearance throughout repeated use. Additionally, use of the aqueous composition on dental appliances will prevent build up (e.g., "white build-up," dental calculus) from collecting or accumulating on the appliances.

Regular and repeated daily use of the aqueous composition on dental appliances will improve the longevity of the appliances and preserve the integrity of the plastic portions of the appliance and the overall cosmetic appearance of the appliance (e.g., maintaining the transparent appearance, minimizing stains and accumulation of build-up, minimizing potential unpleasant smells associated with used appliances).

An aqueous composition for use in cleaning dental appliances is contemplated in this disclosure. As mentioned in the Background, many cleaning and maintenance methods are time consuming and may harm the appliance.

The present invention contemplates a method of cleaning dental appliances with an aqueous composition comprising a surfactant, a flavor additive, a solvent, a preservative and/or antibacterial, and a buffering agent, wherein the volume of aqueous composition used is about 30 uL to 5000 uL and is topically applied to the dental appliance for at least about a few seconds (or until uniformly dispersing the aqueous composition over the appliance). The aqueous composition can also contain sweeteners and/or dyes. This method of cleaning dental appliances ensures prevention of the accumulation of dental plaque and dental calculus or other debris that interferes with the integrity of the plastic and cosmetic appearance of the dental appliance.

The present invention contemplates a method for maintaining and preserving a clean dental appliances that requires a only small amount of aqueous cleanser, less than five (5) ml.

The present invention also contemplates a method for cleaning, maintaining, and preserving dental appliances using the aqueous cleanser that requires a short amount of contact time of less than ten (10) minutes to effectively cleanse the appliance.

In one of the embodiments of the invention the composition comprises water, a surfactant, a flavor additive, a solvent, a preservative, and a buffering agent.

In another embodiment, the composition further comprises a chelating agent.

In one of the embodiments, the surfactant serves as the primary cleansing agent. Sodium lauryl sulfate, also known as SDS, may be used as a surfactant in the present invention. The aqueous composition may contain about 5.5% by weight of surfactant (e.g., sodium lauryl sulfate). Preferably, the surfactant or surfactants comprise between about 1% and about 10% by weight of the composition, and most preferably, the surfactant or surfactants comprise between about 5% and about 6% by weight of the composition. Other preferred surfactants include, but are not limited to, lauryl glucoside, sodium lauroyl sarcosinate, cocamidopropyl betaine, sodium coco-sulfate, sodium laureth sulfate, sodium myreth sulfate, ammonium lauryl sulfate, potassium lauryl sulfate, or sodium pareth sulfate. Surfactants may be used alone or in combination with one another.

In one of the preferred embodiments of the aqueous cleanser composition, the flavor additives used include natural flavorings such as spearmint, peppermint, or wintergreen. In this preferred embodiment, these natural flavorings in total comprise about 0.6% by weight of the composition. The preferred embodiment also utilizes a sweetener. In one of the preferred embodiments, the sweetener is an artificial sweetener, sodium saccharin. In the preferred embodiment, the sodium saccharin comprises 0.5% by weight of the composition. Preferably, the flavor additives comprise between about 0.1% and about 2% by weight of the composition, and most preferably, the flavor additives comprise about 1% by weight of the composition. Other flavor additives may include, but are not limited to, methyl salicylate, cyclohexyl salicylate, menthol, eucalyptus, sorbitol, sucralose, xylitol, stevia, aspartame, neotame, acesulfame potassium, lacitol, maltitol, erythritol, mannitol, isomalt, alitame, cyclamate, neohesperidin dihydrochalcone, or saccharin. Flavor additives may be used alone or in combination with one another.

In one of the preferred embodiments of the aqueous cleanser composition, the solvent used is glycerol. In this preferred composition, the glycerol comprises about 1.4% by weight of the composition. Preferably, the solvents comprise between about 0.1% and about 3% by weight of the composition, and most preferably, the solvents comprise about 1.5% by weight of the composition. Other solvents may include, but are not limited to propylene glycol, polypropylene glycol, propylene carbonate, polysorbates, or sorbitan esters. Solvents may be used alone or in combination with one another.

In one of the preferred embodiments of the aqueous cleanser composition, the antibacterials and preservatives used are potassium sorbate and sodium benzoate. In this preferred composition, the potassium sorbate and the sodium benzoate each comprise about 1% by weight of the composition. Preferably, the preservatives comprise between about 0.1% and about 4% by weight of the composition, and most preferably, the preservatives comprise about 2% by weight of the composition. Other preservatives may include, but are not limited to, triclosan, chlorhexidine, gluconate, polyaminopropyl biguanide, benzalkonium chloride, methylparaben, sodium methylparaben, propylparaben, sodium propylparaben, ethylparaben, sodium ethylparaben, heptylparaben, chloroxylenol, EDTA, phenoxyethanol, octenidine dihydrochloride, thymol, sorbic acid, sodium sorbate, calcium sorbate, benzoic acid, calcium benzoate, potassium benzoate, or hexamine. Preservatives and antibacterials may be used alone or in combination with one another.

In one of the preferred embodiments of the aqueous cleanser composition, the buffering agent used is sodium citrate and citric acid. In this preferred composition, the sodium citrate comprises about 0.5% by weight and the citric acid comprises about 0.05% by weight. Preferably, the buffering agents comprise between about 0.01% and about 1% by weight of the composition, and most preferably, the buffering agents comprise about 0.5% by weight of the composition. Other buffering agents may include, but are not limited to, disodium pyrophosphate, sodium lactate, calcium lactate, magnesium lactate, potassium citrate, calcium citrate, monosodium tartrate, potassium malate, succinic acid, or dipotassium phosphate. Buffering agents may be used alone or in combination with one another.

In one of the preferred embodiments of the aqueous cleanser composition, a chelating agent is also used. In this preferred embodiment, the chelating agent is citric acid, which comprises about 0.05% by weight of the composition.

The aqueous cleanser composition may also include a dye. As noted before, strong dyes may discolor and compromise the appliance's clarity and invisibility. In one of the preferred embodiments of the invention, the dye does not exceed 10 parts per million (0.00001%) by weight. Dyes may include, but are not limited to, any FD&C colors, any D&C colors, or any E-number coded substances approved as food additives by the European Union.

A near-neutral pH is preferred for the aqueous composition, as strongly acidic or basic substances are thought to be harmful to the teeth, gums, and mouth of the user as well as to the plastic and components of the dental appliance being cleaned. One of the preferred embodiments of this invention has a pH of between about 5 and about 9, while the most preferred embodiment has a pH of about 6.2.

The present invention also contemplates a method for cleaning, maintaining, and preserving the integrity and cosmetic appearance of dental appliances using an aqueous cleanser that contains non-toxic and/or natural ingredients. Non-toxic ingredients include those approved by the FDA or similar agencies' boards for topical or oral application, oral consumption or exposure. Natural ingredients include chemicals or materials which can be derived from naturally occurring biological substances, or by choice were derived from naturally occurring biological substances. Biological substances includes those substances created by or derived from the biological and metabolic processes of plants, animals, fungi, protists, bacteria, and archaea, and may not be solely available through the technological processes of humankind Use of such ingredients promotes the pleasantness of the smell of the aqueous composition and the taste of the residual aqueous composition on the appliance to the user after application. The use of such ingredients also overcomes the hesitations of the user to employ harsh toxic chemicals in their oral hygiene routine.

The aqueous composition of the present invention can be applied directly into the cavity of the dental appliance and then an applicator is used to disperse the aqueous composition over the surface of the plastic appliance. Depending upon the type of applicator used, a foam may be produced. After application to the dental appliance, the appliance can then be rinsed and either stored or replaced in the user's mouth for regular wear. Alternatively, the aqueous composition can be applied directly to an applicator (e.g., toothbrush) and then be dispersed over the surface of the plastic appliance (by e.g., brushing) which may result in a foam over the surface of the dental appliance. The appliance can then be rinsed and either stored or replaced in the user's mouth for regular wear.

Generally, the aqueous composition of the present invention can be formulated as an aqueous liquid solution for direct application in drops or with an applicator to the plastic appliance or as a gel or paste composition (e.g., having higher viscosity than aqueous liquid) to be applied to the plastic appliance directly or with an applicator. Additional viscosity agents and lubricating agents or binder/cothickeners (stabilizing agents) can be employed to yield a thicker composition with the same cleansing properties and ease of use. The present invention can be formulated as a more viscous solution or paste-like composition to e.g., provide an additional cleansing method for dentures, implants, or dental appliances with harder plastic components.

The aqueous composition of the present invention can be packaged and stored in a bottle or container with a dropper or a spray apparatus. The composition can also be packaged in a larger volume, for example to provide enough volume for soaking the dental appliance over longer periods of time to cleanse it.

The above-cited patents and patent publications are hereby incorporated by reference in their entirety. Although various embodiments have been described with reference to a particular arrangement of parts, features, and the like, these are not intended to exhaust all possible arrangements or features, and indeed many other embodiments, modifications, and variations will be ascertainable to those of skill in the art. Thus, it is to be understood that the invention may therefore be practiced otherwise than as specifically described above.

EXAMPLE 1

Aqueous Composition for Cleaning Dental Appliances

An aqueous composition used for daily, topical application to a dental appliance using a volume of 40-5000 uL and exposing the plastic portions of the dental appliance to the aqueous composition for at least about 1 second (or until uniformly dispersing the aqueous composition over the appliance). The aqueous composition comprising at least the following:
  1% to about 10% by weight of surfactant; and
  0.1% to about 4% by weight of preservative or antibacterial.

EXAMPLE 2

Aqueous Composition for Cleaning Dental Appliances

An aqueous composition used for daily, topical application to a dental appliance using a volume of 40-5000 uL and exposing the plastic portions of the dental appliance to the aqueous composition for at least about 1 second (or until uniformly dispersing the aqueous composition over the appliance). The aqueous composition comprising:
  1% to about 10% by weight of surfactant;
  0.1% to about 2% by weight of flavor additive;
  0.1% to about 3% by weight of solvent;
  0.1% to about 4% by weight of preservative or antibacterial;
  0.01% to about 1% by weight of buffering agent;
  0.1% and about 2% sweetener; and
  about 0.000001% dye.

EXAMPLE 3

Aqueous Composition for Cleaning Dental Appliances

An aqueous composition used for daily, topical application to a dental appliance using a volume of 50-100 uL and exposing the plastic portions of the dental appliance to the aqueous composition for at least about 1 second or after uniformly dispersing the aqueous composition over the plastic surface of the appliance with an applicator. The aqueous composition comprising:
  5.5% sodium lauryl sulfate;
  1.4% glycerol;

1.0% potassium sorbate;
1.0 sodium benzoate;
0.5% sodium saccharin;
0.6% natural flavors;
0.5% sodium citrate;
0.05% citric acid; and
0.000001% dye

EXAMPLE 4

Cleaning Dental Appliances with Aqueous Composition

The aqueous composition of the present invention can be dispensed from a 1-2 oz. storage bottle onto the user's dental appliance, after the appliance is given a warm water rinse. Two to three (2-3) drops (assuming 40 drops/1 mL), is dispensed from the storage bottles and applied to the cavity of the appliance or onto an applicator (e.g., toothbrush). The aqueous composition is then dispersed over the plastic surface of the appliance with the applicator to generate cleansing foam. The aqueous composition can be rinsed immediately after being dispersed or can be left on the appliance for a period of time, followed by rinsing. Upon rinsing, the appliance can be stored or immediately worn by the user.

What is claimed is:

1. A method of cleaning a dental appliance comprising the steps of:
    a) providing a dental appliance;
    b) contacting the dental appliance with from about 25 µL to about 200 µL of an aqueous composition in liquid form, the aqueous composition consisting essentially of:
        i. from about 5% to about 6% by weight surfactant;
        ii. about 1.5% by weight solvent;
        iii. about 2% by weight antibacterial or preservative; and
        iv. from about 0.1% to about 2% by weight flavor additive;
    c) dispersing the aqueous composition over the dental appliance in liquid form; and
    d) rinsing the dental appliance with water.

2. The method of claim 1, wherein the aqueous composition is non-toxic.

3. The method of claim 1, wherein the surfactant comprises sodium lauryl sulfate, lauryl glucoside, sodium lauroyl sarcosinate, cocamidopropyl betaine, sodium cocosulfate, sodium laureth sulfate, sodium myreth sulfate, ammonium lauryl sulfate, potassium lauryl sulfate, or sodium pareth sulfate.

4. The method of claim 1, wherein the aqueous composition comprises about 5.5% by weight sodium lauryl sulfate.

5. The method of claim 1, wherein the solvent comprises glycerol, propylene glycol, polypropylene glycol, propylene carbonate, polysorbates, sorbitan esters and combinations thereof.

6. The method of claim 1, wherein the antibacterial or preservative comprises potassium sorbate, sodium benzoate, triclosan, chlorhexidine, gluconate, polyaminopropyl biguanide, benzalkonium chloride, methylparaben, sodium methylparaben, propylparaben, sodium propylparaben, ethylparaben, sodium ethylparaben, heptylparaben, chloroxylenol, EDTA, phenoxyethanol, octenidine dihydrochloride, thymol, sorbic acid, sodium sorbate, calcium sorbate, benzoic acid, calcium benzoate, potassium benzoate, hexamine and combinations thereof.

7. The method of claim 1, wherein the aqueous composition comprises about 1% potassium sorbate and about 1% sodium benzoate.

8. The method of claim 1, wherein the aqueous composition further comprises about 0.5% by weight of a buffering agent comprising sodium citrate, disodium pyrophosphate, sodium lactate, calcium lactate, magnesium lactate, potassium citrate, calcium citrate, monosodium tartrate, potassium malate, succinic acid, dipotassium phosphate, and combinations thereof.

9. The method of claim 1, further comprising a dye, wherein the dye does not exceed 10 parts per million by weight.

10. The method of claim 1, wherein the aqueous composition is applied to the dental appliance daily.

11. The method of claim 1, wherein the aqueous composition is dispersed on the dental appliance using a toothbrush.

12. The method of claim 1, wherein the dental appliance is effectively cleaned in less than 10 minutes.

13. The method of claim 1, wherein the composition does not contain abrasives.

14. The method of claim 1, wherein the composition does not contain allergenic persulphates or bleach.

15. The method of claim 1, wherein the composition does not impede or deteriorate the dental appliance.

16. The method of claim 1, the aqueous composition comprising:
    i. about 5.5% by weight sodium lauryl sulfate;
    ii. about 1.5% by weight glycerol;
    iii. about 1% by weight sodium benzoate;
    iv. about 1% by weight potassium sorbate; and
    v. from about 0.1% to about 2% by weight flavor additive.

* * * * *